(12) United States Patent
Yasunaga

(10) Patent No.: US 9,504,515 B2
(45) Date of Patent: Nov. 29, 2016

(54) TREATMENT DEVICE

(71) Applicant: OLYMPUS CORPORATION, Tokyo (JP)

(72) Inventor: Shinji Yasunaga, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 279 days.

(21) Appl. No.: 14/084,765

(22) Filed: Nov. 20, 2013

(65) Prior Publication Data

US 2014/0074087 A1   Mar. 13, 2014

Related U.S. Application Data

(63) Continuation of application No. PCT/JP2012/062946, filed on May 21, 2012.

(30) Foreign Application Priority Data

May 24, 2011   (JP) ................. 2011-116101

(51) Int. Cl.
*A61B 18/18* (2006.01)
*A61B 18/12* (2006.01)
(Continued)

(52) U.S. Cl.
CPC ....... *A61B 18/1206* (2013.01); *A61B 18/1445* (2013.01); *A61B 18/085* (2013.01);
(Continued)

(58) Field of Classification Search
CPC  A61B 18/085; A61B 18/10; A61B 18/1206; A61B 18/1445; A61B 2018/00196; A61B 2018/00595; A61B 2018/00601; A61B 2018/00642; A61B 2018/00702; A61B 2018/00797; A61B 2018/00821; A61B 2018/1455
See application file for complete search history.

(56) References Cited

U.S. PATENT DOCUMENTS 8,808,161 B2 *   8/2014   Gregg et al. .................... 600/34
2002/0082593 A1 *   6/2002   Hareyama ............ A61B 18/085
606/38

(Continued)

FOREIGN PATENT DOCUMENTS

JP   2002-238916 A   8/2002
JP   2006-325916 A   12/2006

(Continued)

OTHER PUBLICATIONS

International Search Report dated Jun. 12, 2012 issued in PCT/JP2012/062946.

*Primary Examiner* — Michael Peffley
*Assistant Examiner* — Amanda Zink
(74) *Attorney, Agent, or Firm* — Scully, Scott, Murphy & Presser, P.C.

(57) ABSTRACT

A treatment device treats a biotissue by heating the biotissue to a target temperature. The device includes a heat-transfer member conveying heat to the biotissue, a heat-generating chip including a heat-generating member, a first temperature-measuring module, a temperature-measuring element disposed on the heat-transfer member, a second temperature-measuring module, and a controller. The heat-generating member heats the heat-transfer member. The first temperature-measuring module obtains a first temperature of the heat-generating member. The second temperature-measuring module obtains a second temperature measured by the temperature-measuring element. The controller determines the supplied electric power based on the first temperature after start of heating and before a transition point in time, and based on the second temperature after the transition point in time.

6 Claims, 15 Drawing Sheets

(51) Int. Cl.
*A61B 18/14* (2006.01)
*A61B 18/08* (2006.01)
*A61B 18/10* (2006.01)
*A61B 18/00* (2006.01)

(52) U.S. Cl.
CPC ..... *A61B 18/10* (2013.01); *A61B 2018/00196* (2013.01); *A61B 2018/00595* (2013.01); *A61B 2018/00601* (2013.01); *A61B 2018/00642* (2013.01); *A61B 2018/00702* (2013.01); *A61B 2018/00797* (2013.01); *A61B 2018/00821* (2013.01); *A61B 2018/1455* (2013.01)

(56) References Cited

U.S. PATENT DOCUMENTS

| | | | |
|---|---|---|---|
| 2008/0009854 A1* | 1/2008 | Yates | 606/42 |
| 2008/0281312 A1 | 11/2008 | Werneth et al. | |
| 2008/0281322 A1* | 11/2008 | Sherman et al. | 606/42 |

FOREIGN PATENT DOCUMENTS

| | | |
|---|---|---|
| JP | 2009-247893 A | 10/2009 |
| JP | 2010-526641 A | 8/2010 |

\* cited by examiner

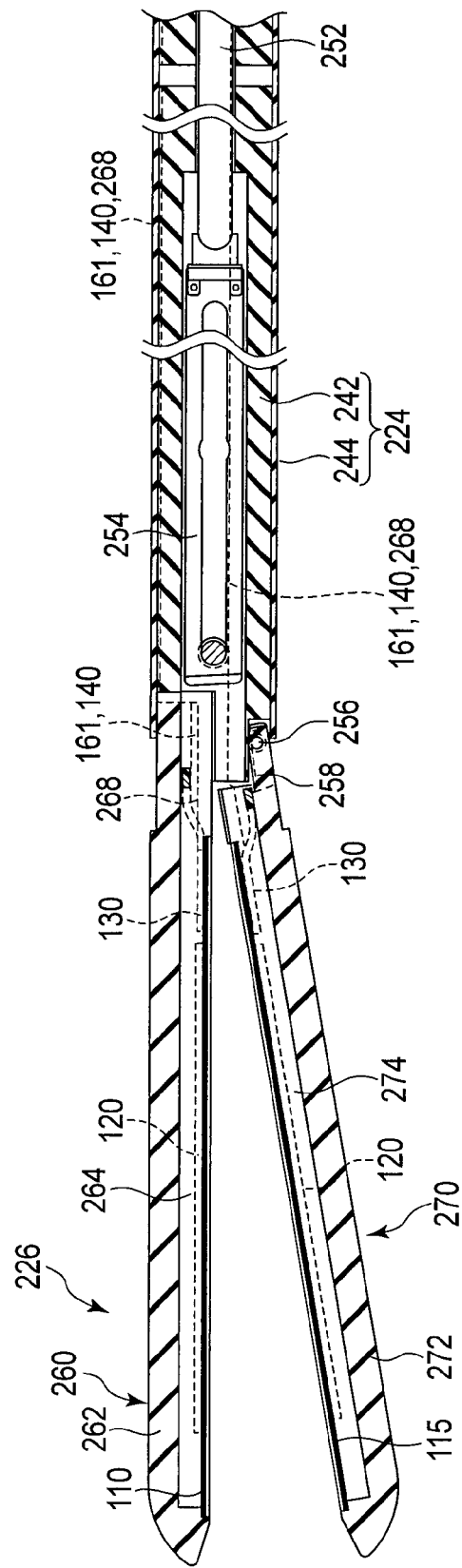
F I G. 2B

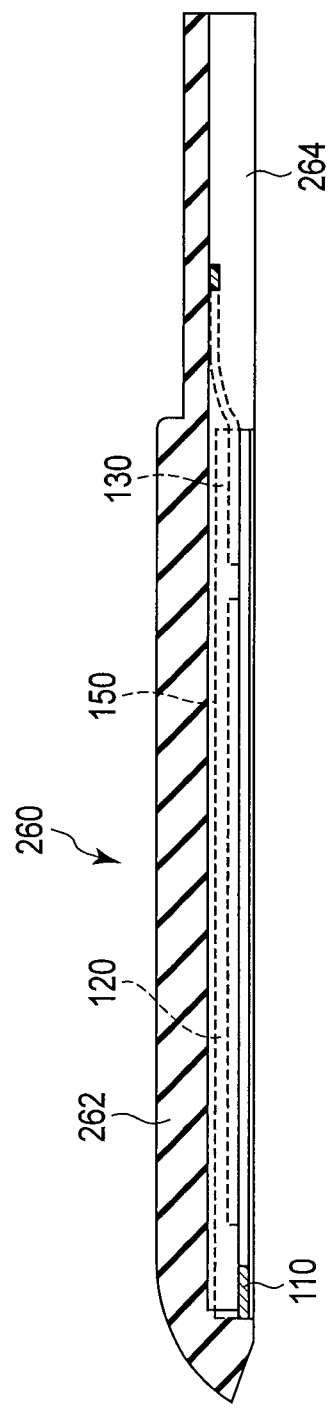
F I G. 3B

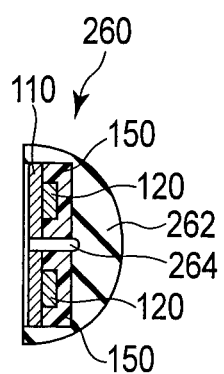
F I G. 3C

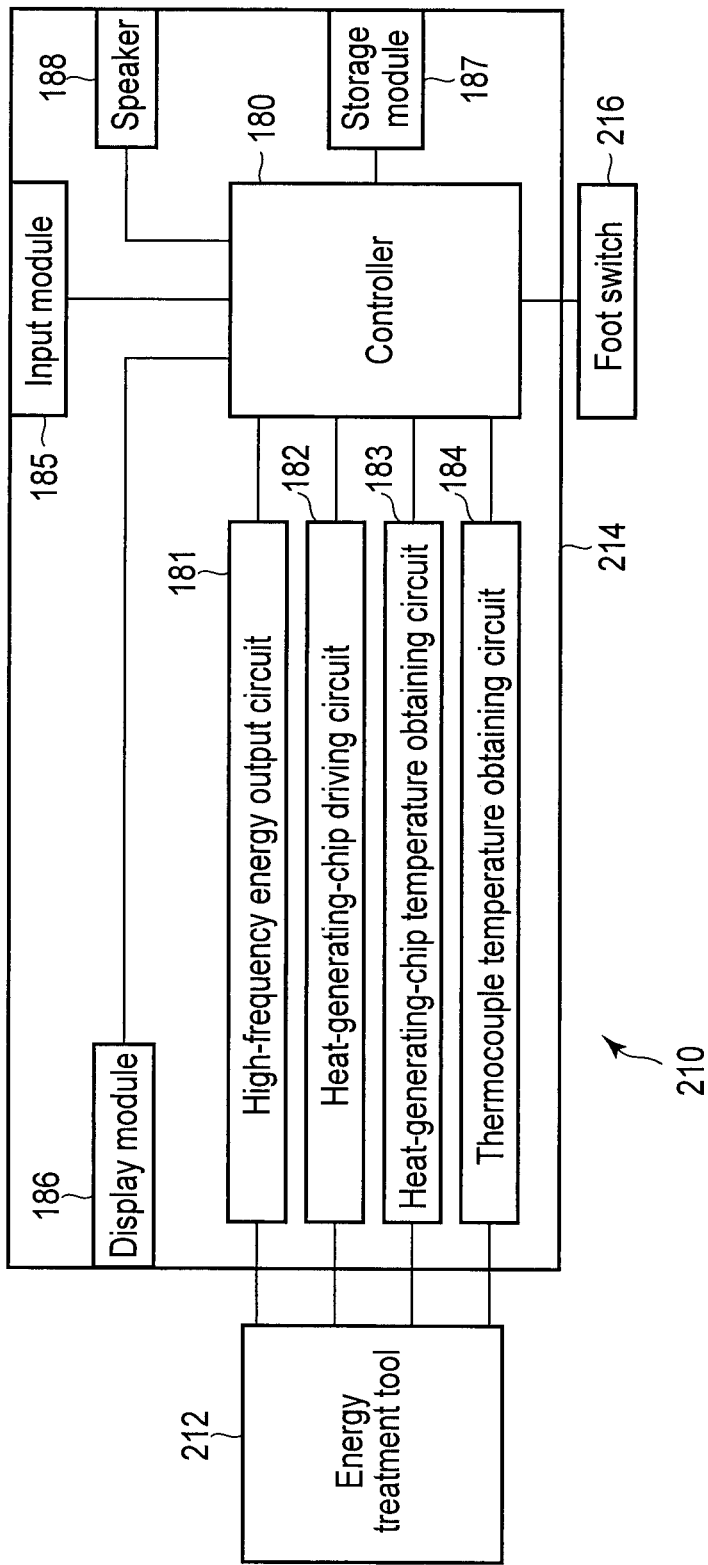
F I G. 7

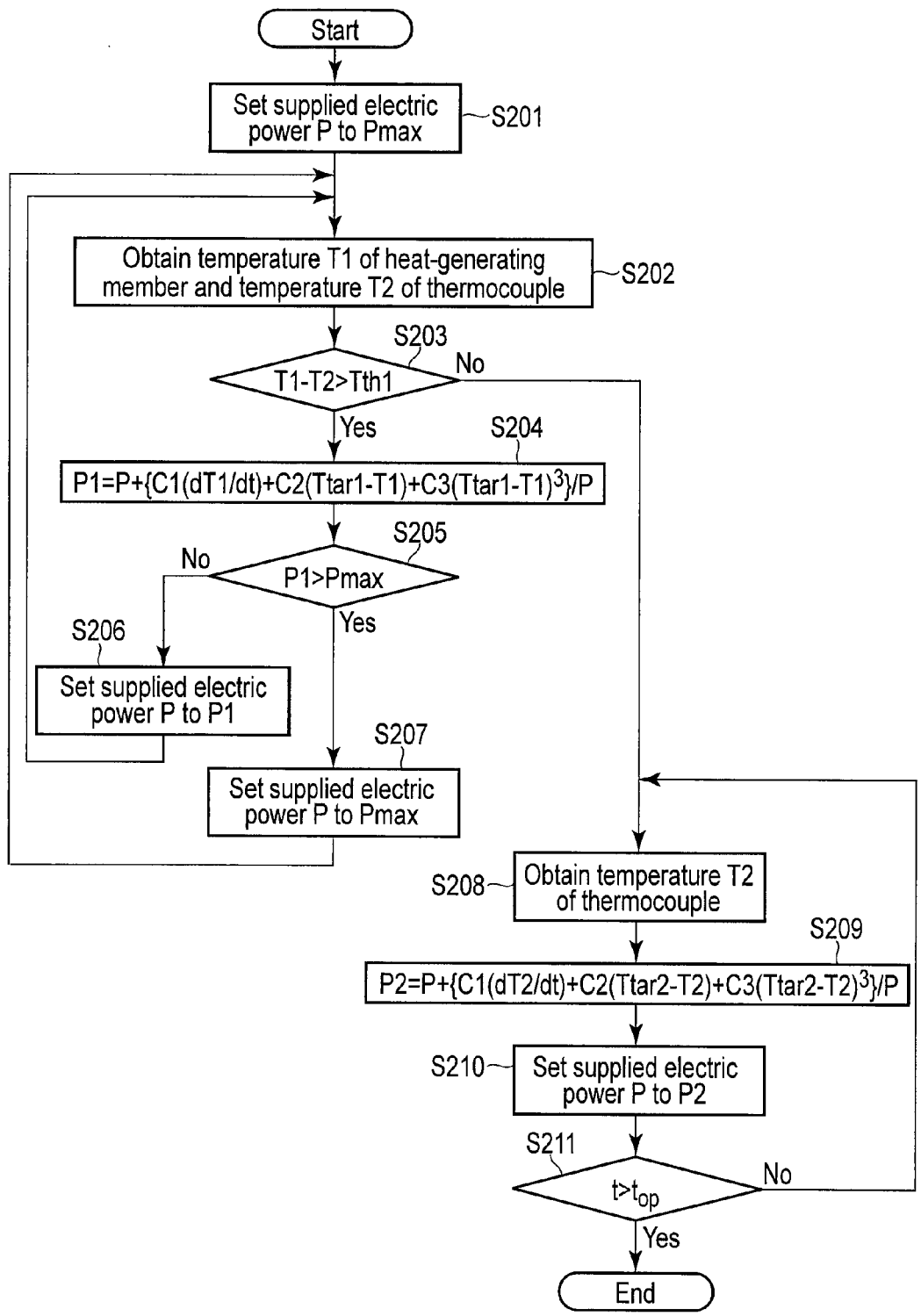
F I G. 10

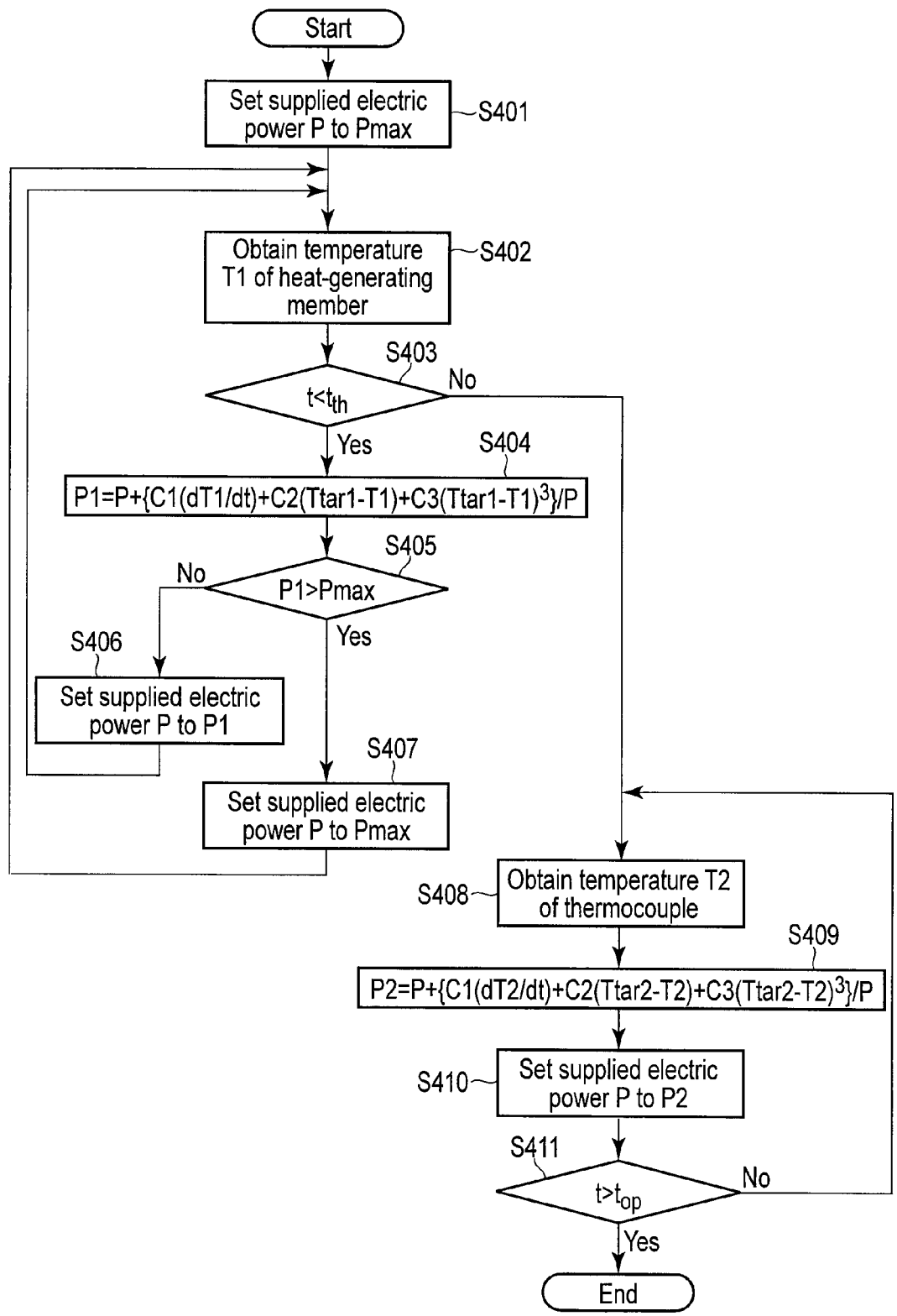
F I G. 12

TREATMENT DEVICE

CROSS-REFERENCE TO RELATED APPLICATIONS

This application is a Continuation application of PCT Application No. PCT/JP2012/062946, filed May 21, 2012 and based upon and claiming the benefit of priority from prior Japanese Patent Application No. 2011-116101, filed May 24, 2011, the entire contents of all of which are incorporated herein by reference.

BACKGROUND OF THE INVENTION

1. Field of the Invention

The present invention relates to a treatment device.

2. Description of the Related Art

Generally, treatment devices for treating biotissues by using high-frequency energy and thermal energy are known. For example, Jpn. Pat. Appln. KOKAI Pub. No. 2009-247893 discloses the following treatment device. Specifically, the treatment device includes an openable/closable holder for holding a biotissue to be treated. A part of the holder contacting the biotissue is provided with a high-frequency electrode to apply a high-frequency voltage and a heat-generating chip to heat the high-frequency electrode. In addition, the holder is provided with a cutter. When such a treatment device is used, first, the biotissue is held with the holder, and a high-frequency voltage is applied to the biotissue. Then, the biotissue is heated by the holder, and thereby the biotissue is anastomosed. It is also possible to perform excision by a cutter attached to the holder, in a state where the biotissue end portion is inosculated.

To perform stable biotissue anastomosis in a treatment device as disclosed in Jpn. Pat. Appln. KOKAI Pub. No. 2009-247893, it is necessary to control a temperature of a heat-transfer member contacting the biotissue, such as the electrode of the above holder, with high accuracy. In addition, it is required to increase the temperature of the heat-transfer member to a desired temperature in a short time from the start of heating. To increase the temperature of the heat-transfer member with a small heat-generating chip in a short time, it is necessary to supply much electric power to the heat-generating chip at an early stage of heating. As a result, the heat flux density from the heat-generating chip to the heat-transfer member becomes very large, and a difference in temperature between the heat-generating chip and the heat-transfer member increases.

For example, when the heat-transfer member is provided with a temperature sensor and the electric power supplied to the heat-generating chip is controlled based on the temperature of the heat-transfer member measured by the temperature sensor, the temperatures of the heat-generating chip and surrounding members may be increased to a temperature enough to break them, due to the difference in temperature between the heat-generating chip and the heat-transfer member. It is also possible to obtain the temperature of the heat-generating member without using the temperature sensor on the heat-transfer member. For example, it is possible to obtain the temperature of the heat-generating member, based on a change in a resistance of the heat-generating member of the heat-generating chip. The heat-generating chip or the like can be prevented from being broken by controlling the temperature of the heat-transfer member based on the temperature obtained as described above. To achieve this structure, however, it is necessary to reduce the individual variation in the resistance of the heat-generating member, and to obtain a relation between the temperature and the resistance in advance with high accuracy, to obtain the temperature of the heat-generating chip with high accuracy. This increases the cost of the whole system.

BRIEF SUMMARY OF THE INVENTION

The object of the present invention is to provide a treatment device that enables highly accurate control of the temperature for heating a biotissue at small cost and without malfunction.

According to an aspect of the invention, a treatment device is configured to treat a biotissue by heating the biotissue to a target temperature. The device includes a heat-transfer member configured to contact the biotissue at a first principal surface of the heat-transfer member, and convey heat to the biotissue, the first principal surface and a second principal surface serving as front and rear surfaces; a heat-generating chip being connected with the second principal surface at a third principal surface of the heat-generating chip, and configured to heat the heat-transfer member by a supplied electric power supplied to a heat-generating member formed on a fourth principal surface of the heat-generating chip, the third principal surface and the fourth principal surface serving as front and rear surfaces; a first temperature-measuring module configured to obtain a temperature of the heat-generating member as a first temperature; a temperature-measuring element disposed in a region of the heat-transfer member with which the heat-generating chip is not connected; a second temperature-measuring module configured to obtain a temperature measured by the temperature-measuring element as a second temperature; and a controller configured to determine the supplied electric power based on the first temperature obtained by the first temperature-measuring module in a first time region after start of heating and before a transition point in time, and determine the supplied electric power based on the second temperature obtained by the second temperature-measuring module in a second time region after the transition point in time, when the biotissue is heated with the target temperature.

According to the present invention, a supplied electric power is determined based on the first temperature of the heat-generating member obtained by the first temperature-measuring module and the second temperature of the heat-transfer member obtained by the second temperature-measuring module, and thus it is possible to provide a treatment device that enables highly accurate control of the temperature for heating a biotissue at small cost and without malfunction.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2B is a schematic diagram of a cross-sectional view of an example of a structure of the shaft and the holder of the energy treatment tool according to the embodiments, in a state where the holder is opened.

FIG. 3B is a schematic diagram of an example of a structure of the first holding member of the holder according to the embodiments, and is a longitudinal cross-sectional view taken along line 3B-3B illustrated in FIG. 3A.

FIG. 3C is a schematic diagram of an example of a structure of the first holding member of the holder according to the embodiments, and is a lateral cross-sectional view taken along line 3C-3C illustrated in FIG. 3A.

FIG. 7 is a diagram illustrating an example of a configuration of an energy source according to the embodiments.

FIG. 10 is a flowchart of an example of processing performed by a controller according to a second embodiment.

FIG. 12 is a flowchart of an example of processing performed by a controller according to a fourth embodiment.

DETAILED DESCRIPTION OF THE INVENTION

First Embodiment

Figure 1:
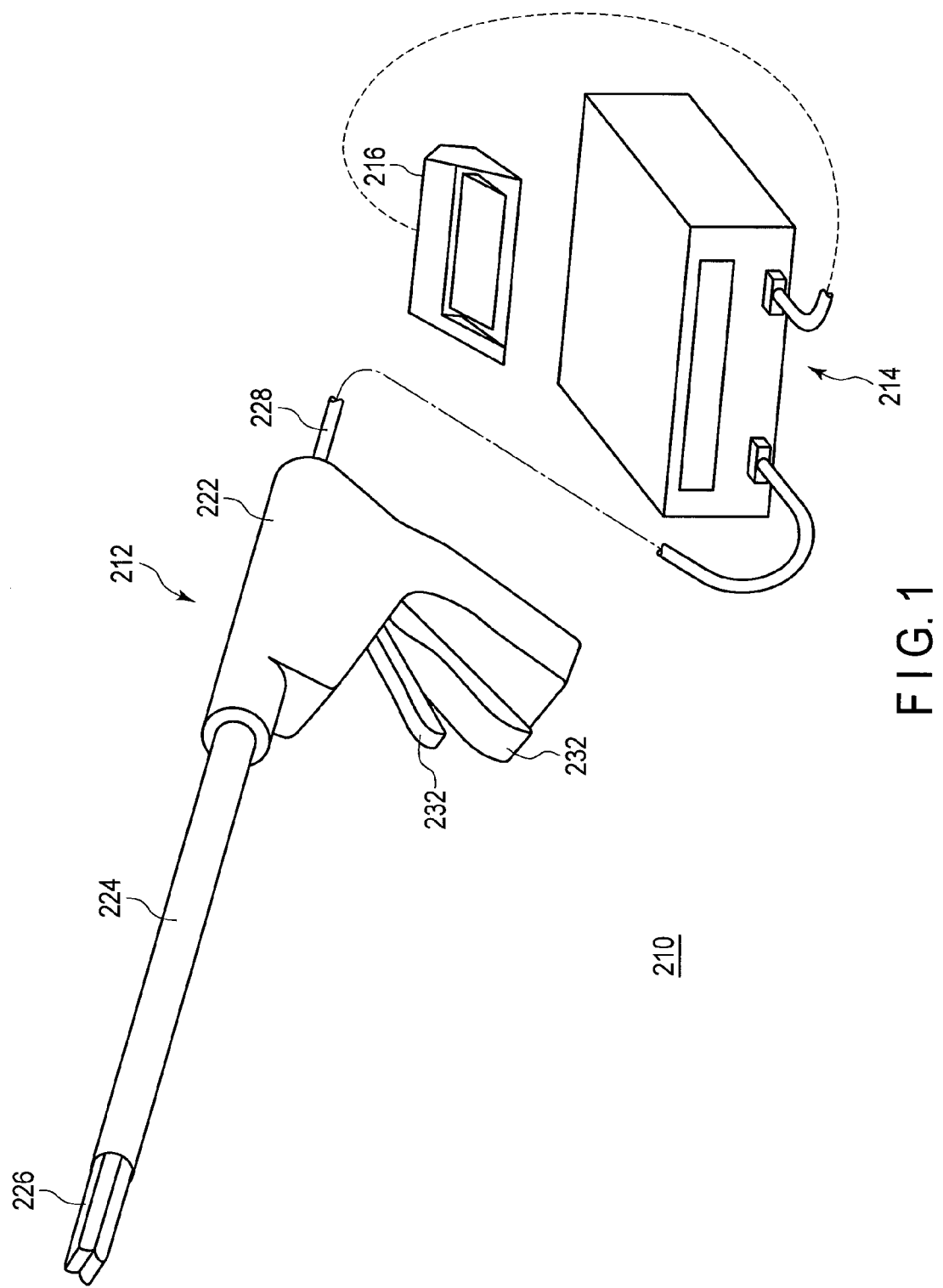
FIG. 1 is a schematic diagram of an example of a structure of a treatment system according to embodiments of the present invention.

A first embodiment of the present invention will now be described with reference to the drawings. A treatment device according to the present embodiment is used for treating biotissues, and causes high-frequency energy and thermal energy to act on the biotissues. As illustrated in FIG. 1, the treatment device 210 includes an energy treatment tool 212, an energy source 214, and a foot switch 216.

The energy treatment tool 212 is a linear-type surgical treatment tool to pierce, for example, the abdominal wall and perform treatment. The energy treatment tool 212 includes a handle 222, a shaft 224 attached to the handle 222, and a holder 226 provided at the distal end of the shaft 224. The holder 226 is a treatment unit that is openable and closable, holds the biotissue to be treated, and performs treatment such as coagulation and incision. In the following explanation, the side of the holder 226 is referred to as "distal end side", and the side of the handle 222 is referred to as "proximal end side", for the sake of explanation. The handle 222 includes a plurality of operating knobs 232 to operate the holder 226. The shape of the energy treatment tool 212 is an example, and the energy treatment tool 212 may have another shape as long as it has a similar function. For example, the energy treatment tool 212 may have a shape like forceps, or the shaft may be curved.

The handle 222 is connected to the energy source 214 via a cable 228. The energy source 214 is connected with the foot switch 216. The foot switch 216 that is operated by foot may be replaced with a hand operated switch or another switch. By the operator operating the pedal of the foot switch 216, energy supply from the energy source 214 to the energy treatment tool 212 is turned on and off.

Figure 2A:
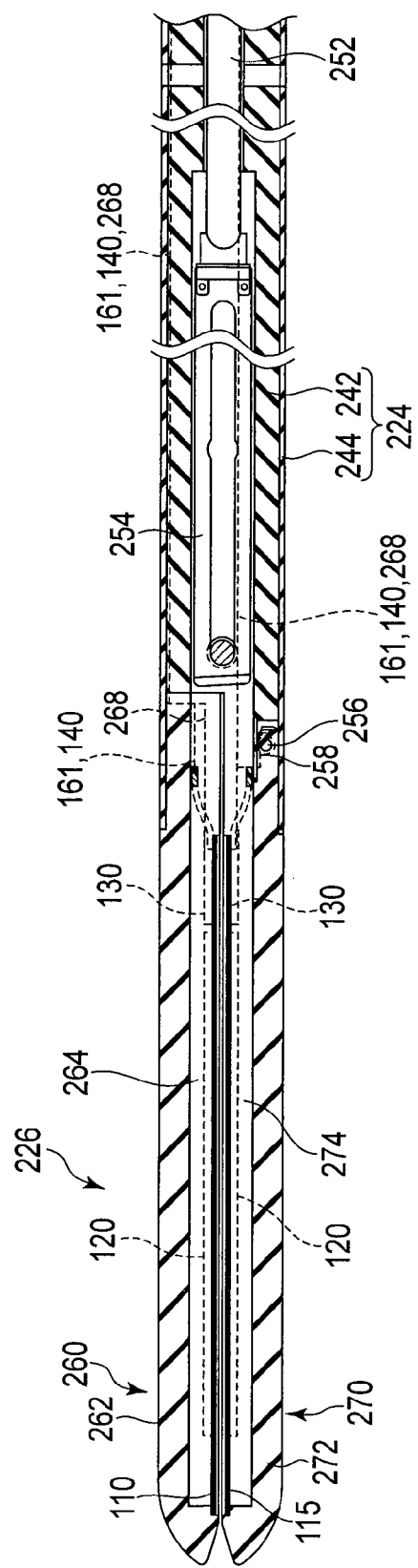
FIG. 2A is a schematic diagram of a cross-sectional view of an example of a structure of a shaft and a holder of an energy treatment tool according to the embodiments, in a state where the holder is closed.

FIG. 2A and FIG. 2B illustrate an example of a structure of the holder 226 and the shaft 224. FIG. 2A illustrates a state where the holder 226 is closed, and FIG. 2B illustrates a state where the holder 226 is opened. The shaft 224 includes a cylindrical member 242 and a sheath 244. The cylindrical member 242 is fixed at its proximal end to the handle 222. The sheath 244 is disposed on the outer circumference of the cylindrical member 242, such that the sheath 244 is slidable along the axial direction of the cylindrical member 242.

The holder 226 is disposed at the distal end portion of the cylindrical member 242. The holder 226 includes a first holding member 260, and a second holding member 270. A proximal portion of the first holding member 260 is fixed to the distal end portion of the cylindrical member 242 of the shaft 224. On the other hand, a proximal portion of the second holding member 270 is rotatably supported on the distal end portion of the cylindrical member 242 of the shaft 224 by a support pin 256. Thus, the second holding member 270 is rotated around the axis of the support pin 256, and opens and closes with respect to the first holding member 260.

In the state where the holder 226 is closed, a cross section obtained by putting the proximal portion of the first holding member 260 and the proximal portion of the second holding member 270 together has a circular shape. The second holding member 270 is urged by an elastic member 258, such as a leaf spring, so as to be opened with respect to the first holding member 260. When the sheath 244 is slid toward the distal end side with respect to the cylindrical member 242 and the proximal portion of the first holding member 260 and the proximal portion of the second holding member 270 by the sheath 244, the first holding member 260 and the second holding member 270 are closed against the urging force of the elastic member 258, as illustrated in FIG. 2A. On the other hand, when the sheath 244 is slid toward the proximal end side of the cylindrical member 242, the second holding member 270 is opened with respect to the first holding member 260 by the urging force of the elastic member 258, as illustrated in FIG. 2B.

The cylindrical member 242 includes a high-frequency electrode conducting wire 268 connected to a first high-frequency electrode 110 or a second high-frequency electrode 115, a heat-generating chip conducting wire 161 connected to a heat-generating chip 120 serving as a heat-generating member, and a thermocouple 140, which are inserted through the cylindrical member 242.

A driving rod 252 connected at its proximal end to one of the operating knobs 232 is disposed inside the cylindrical member 242, such that the driving rod 252 is movable along the axial direction of the cylindrical member 242. A cutter 254 having a thin-plate shape and including a blade at its distal end side is disposed on a distal end side of the driving rod 252. When the operating knob 232 is operated, the cutter 254 is moved along the axial direction of the cylindrical member 242 through the driving rod 252. When the cutter 254 is moved toward the distal end side, the cutter 254 is fitted into cutter-guide grooves 264 and 274 that are formed in the holder 226, as described below.

Figure 3A:
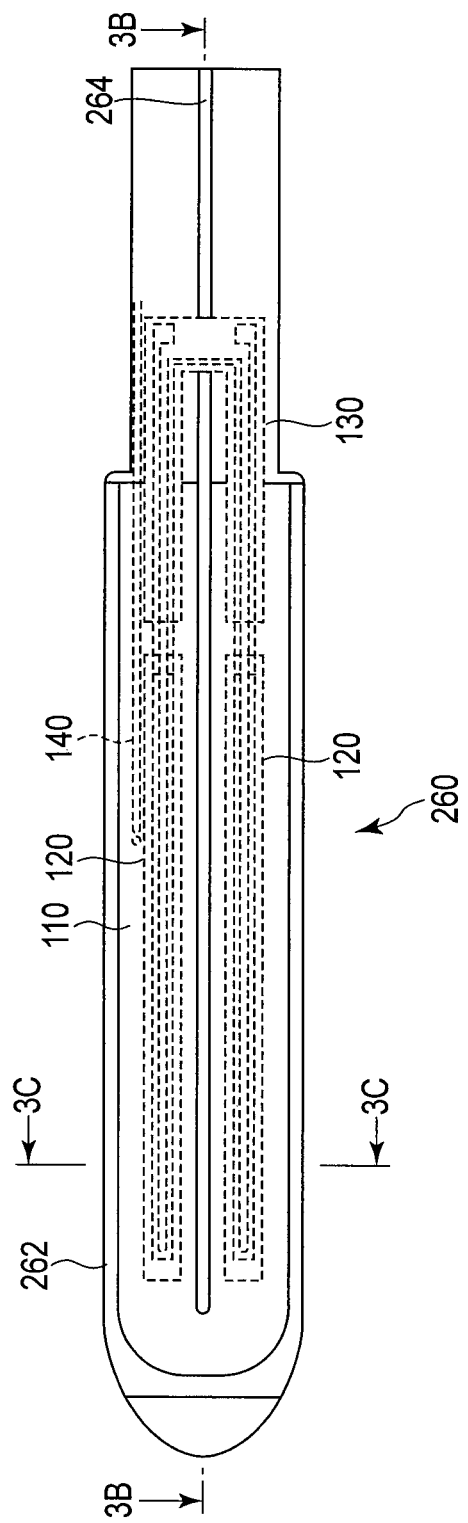
FIG. 3A is a schematic plan view of an example of a structure of a first holding member of the holder according to the embodiments.

The first holding member 260 will now be explained with reference to FIG. 3A, FIG. 3B, and FIG. 3C. FIG. 3A is a plan view of the first holding member 260. FIG. 3B is a longitudinal cross-sectional view of the first holding member 260, taken along line 3B-3B illustrated in FIG. 3A. FIG. 3C is a lateral cross-sectional view of the first holding member 260, taken along line 3C-3C illustrated in FIG. 3A. The first holding member 260 includes a first holding member main body 262, and the second holding member 270 includes a second holding member main body 272. A cutter-guide groove 264 to guide the cutter 254 is formed in the first holding member main body 262. The first holding member main body 262 is provided with a recess, in which a first high-frequency electrode 110 formed of a copper thin plate or the like is disposed. Since the cutter-guide groove 264 exists, the first high-frequency electrode 110 has an almost U shape in plan view. As illustrated in FIG. 2A and FIG. 2B, the high-frequency electrode conducting wire 268 is electrically connected to the first high-frequency electrode 110. The first high-frequency electrode 110 is connected to the cable 228 through the high-frequency electrode conducting wire 268.

The second holding member 270 and the first holding member 260 are symmetrical. Specifically, the second holding member 270 is provided with the cutter-guide groove 274 formed in a position opposed to the cutter-guide groove 264. In addition, the second holding member main body 272 is provided with a second high-frequency electrode 115 disposed in a position opposed to the first high-frequency electrode 110. The second high-frequency electrode 115 is connected to the cable 228 through the high-frequency electrode conducting wire 268.

When the holder 226 in the closed state holds the biotissue, the held biotissue contacts the first high-frequency electrode 110 and the second high-frequency electrode 115. Each of the first holding member main body 262 and the second holding member main body 272 has a unit for generating heat to cauterize the biotissue contacting the first high-frequency electrode 110 and the second high-frequency electrode 115. The heat-generating unit provided on the first holding member main body 262 has the same form as the heat-generating unit provided on the second holding member main body 272. In the following explanation, the heat-generating unit formed in the first holding member main body 262 will be explained as an example.

Figure 4:
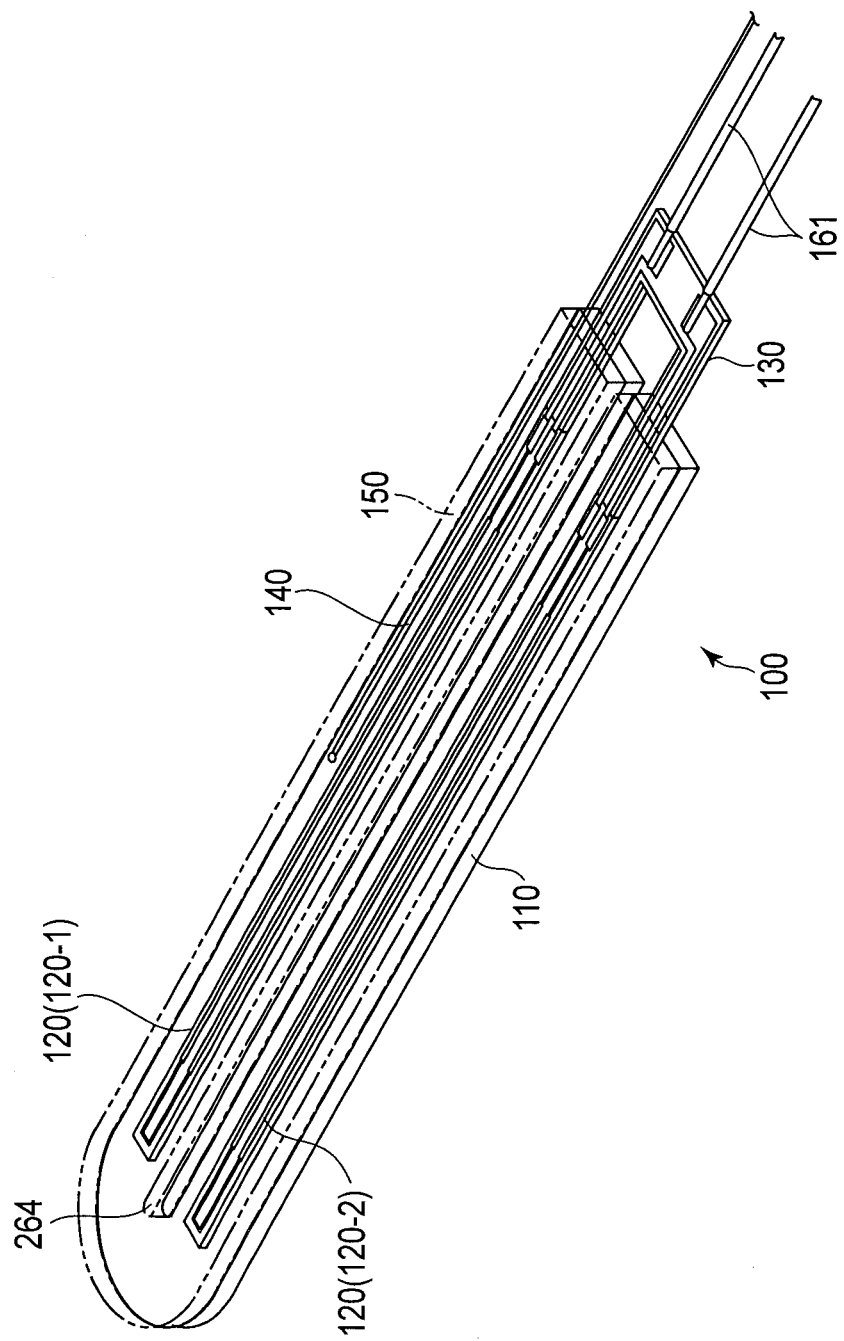
FIG. 4 is a perspective view illustrating an example of a structure of a first heat-generating unit according to the embodiments.

FIG. 4 is a perspective view of a structure of a heat-generating unit 100. The heat-generating unit 100 includes the first-high-frequency electrode 110, two heat-generating chips 120, a flexible board 130, a thermocouple 140, and a sealing film 150. As described above, the U-shaped first high-frequency electrode 110 also functions as a heat-transfer member that transfers heat to the biotissue. The heat-generating chips 120, the flexible board 130, and the thermocouple 140 are arranged on the first high-frequency electrode 110. The sealing film 150 is formed by applying a sealant such as silicone onto the first high-frequency electrode 110 to cover the heat-generating chips 120, the flexible board 130, and the thermocouple 140.

Figure 5:
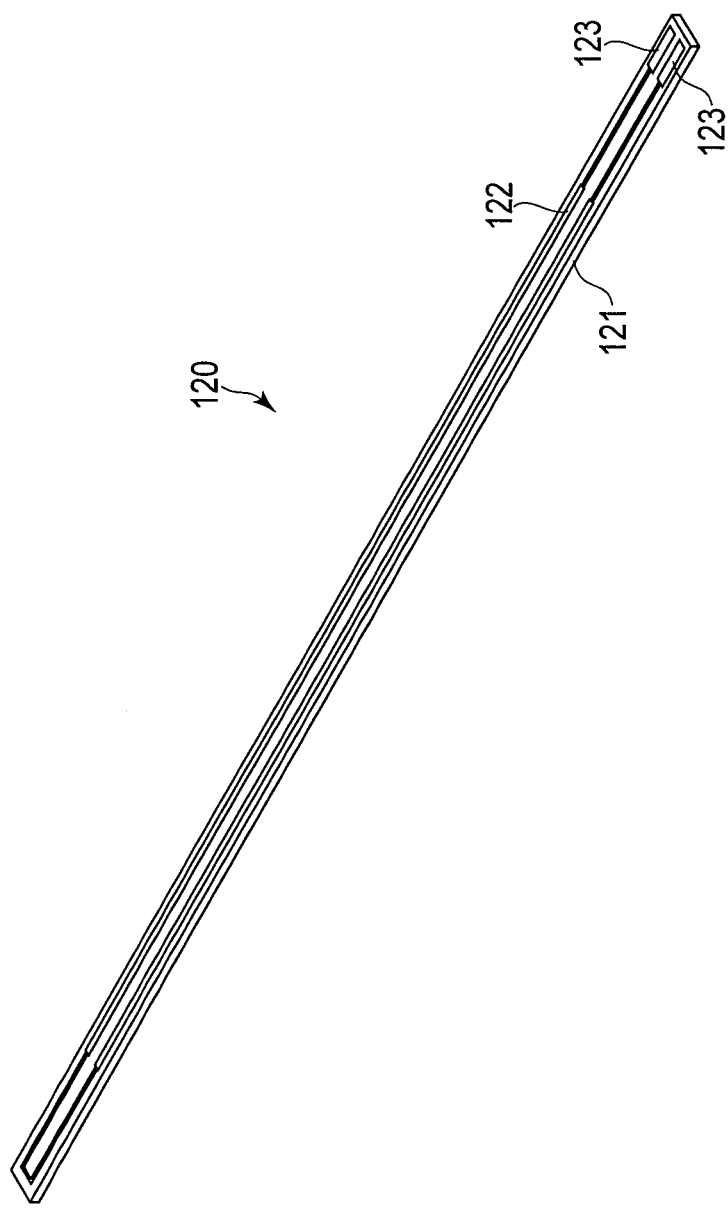
FIG. 5 is a perspective view illustrating an example of a structure of a heat-generating chip according to the embodiments.

FIG. 5 is a perspective view of a structure of the heat-generating chip 120. Each of the heat-generating chip 120 includes a board 121 having an elongated shape and formed of ceramic. A heat-generating member 122, for example, a high-resistant metal thin film, is formed on the board 121. The heat-generating member is formed in an elongated shape from the proximal end side to the distal end side of the board 121, turned at the distal end side to have a U-shape, and further formed to the proximal end side. Specifically, the heat-generating member 122 has a U shape, both ends of which are located on the proximal end side.

Electrode pads 123 are formed side by side in the respective end portions of the heat-generating member 122, which are located on the proximal end side of the heat-generating chip 120. In the heat-generating chip 120, when the voltage is applied between the two electrode pads 123, an electric current flows through the heat-generating member 122, and the heat-generating member 122 generates heat with the electric current.

Figure 6:
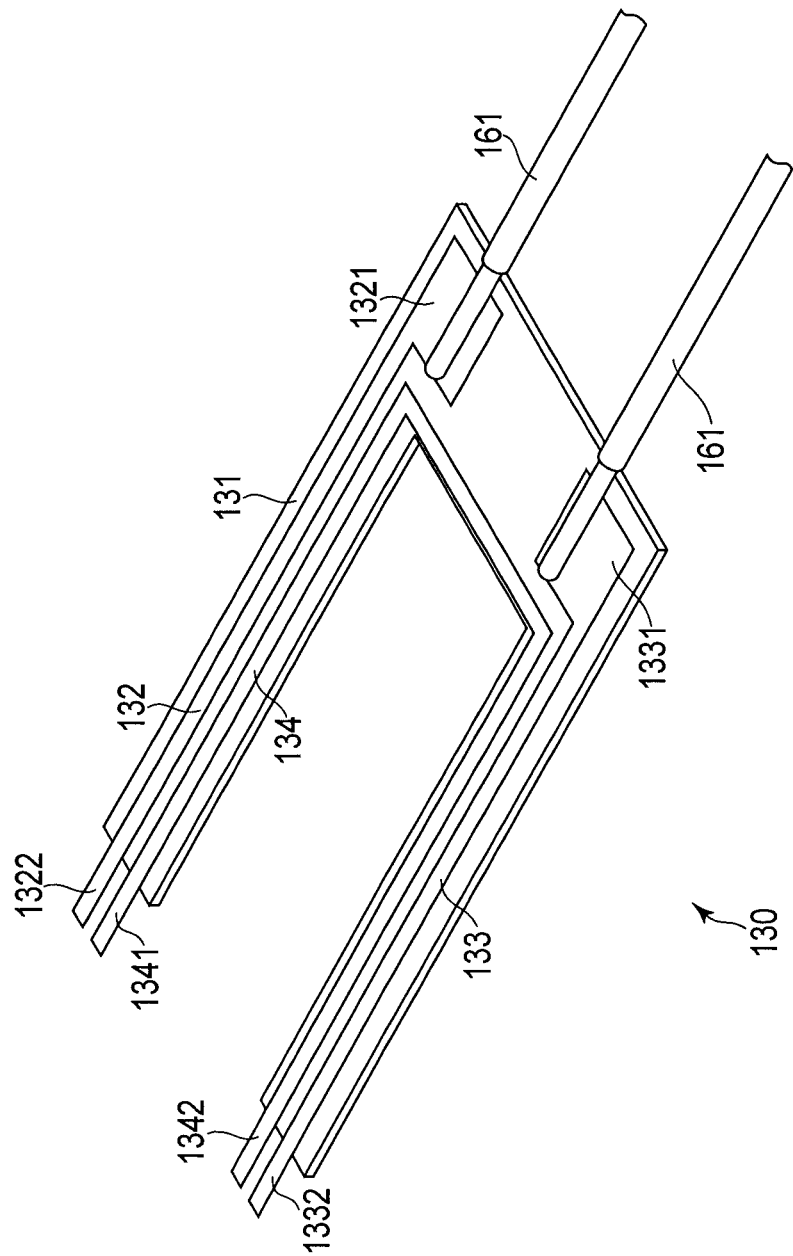
FIG. 6 is a perspective view illustrating an example of a structure of a flexible board according to the embodiments.

FIG. 6 is a perspective view of a structure of the flexible board 130. The flexible board 130 includes a base member 131 formed of polyimide or the like. The base member 131 has, for example, a U shape. The base member 131 is disposed such that a bottom portion of the U shape is located on the proximal end side and the end portions being the upper portion of the U shape are located toward the distal end side. A first wire 132, a second wire 133, and a third wire 134, which are copper-foil wires, are formed on the base member 131. The first wire 132 includes a first connecting pad portion 1321 on the proximal end side of the base member 131. The first wire 132 also includes a first flying lead portion 1322 formed to extend outside the base member 131 on the distal end side of the base member 131.

In the same manner, the second wire 133 is formed in a symmetrical shape with respect to the first wire 132. Specifically, the second wire 133 includes a second connecting pad portion 1331 on the proximal end side of the base member 131. The second wire 133 also includes a second flying lead portion 1332 formed to extend outside the base member 131, at an end on the distal end side of the base member 131, which is different from the end from which the first flying lead portion 1322 projects. As described above, the first flying lead portion 1322 and the second flying lead portion 1332 project from respective ends of the U-shape of the base member 131.

The third wire 134 is formed in a U shape along the shape of the base member 131. The third wire 134 includes a third flying lead portion 1341 disposed adjacent to the first flying lead portion 1322, and a fourth flying lead portion 1342 disposed adjacent to the second flying lead portion 1332.

As illustrated in FIG. 4, the flexible board 130 is disposed on the proximal end side of the first high-frequency electrode 110, and both ends thereof are arranged to hold the cutter-guide groove 264 therebetween. The both end portions of the U shape of the flexible board 130 are arranged on the first high-frequency electrode 110, and the bottom portion of the U shape projects to the proximal end side of the first high-frequency electrode 110. The flexible board 130 is disposed such that the base member 131 contacts a second principal surface of the first high-frequency electrode 110.

The two heat-generating chips 120, that is, the first heat-generating chip 120-1 and the second heat-generating chip 120-2 are arranged in symmetrical positions holding the cutter-guide groove 264 of the first high-frequency electrode 110 therebetween, such that the longitudinal directions of the chips agree with the longitudinal direction of the first high-frequency electrode 110. In this arrangement, the heat-generating chips 120 are fixed by soldering or the like, such that their boards 121 contact the second principal surface of the first high-frequency electrode 110.

One of the two electrode pads 123 of the first heat-generating chip 120-1 is connected with the first flying lead portion 1322 of the flexible board 130, and the other is connected with the third flying lead portion 1341. One of the two electrode pads 123 of the second heat-generating chip 120-2 is connected with the second flying lead portion 1332 of the flexible board 130, and the other is connected with the fourth flying lead portion 1342.

One of a pair of heat-generating chip conducting wires 161 is connected with the first connecting pad portion 1321 of the flexible board 130, and the other of the heat-generating chip conducting wires 161 is connected with the second connecting pad portion 1331. The heat-generating chip conducting wires 161 are connected to the energy source 214 through the cable 228.

As described above, the first wire 132, the heat-generating member 122 of the first heat-generating chip 120-1, the third wire 134, the heat-generating member 122 of the second heat-generating chip 120-2, and the second wire 133 are connected in this order in series between a pair of heat-generating chip conducting wires 161. Thus, an electric current output from the energy source 214 flows through the heat-generating members 122 of the two first heat-generating chips 120. As a result, each heat-generating member 122 generates heat. When the heat-generating members 122 generate heat, the heat is conveyed to the first high-frequency electrode 110. The biotissue contacting the first high-frequency electrode 110 is cauterized by the heat.

The thermocouple 140 is disposed on the first high-frequency electrode 110. The thermocouple 140 is connected to the energy source 214 through the cable 228. The thermocouple 140 is used to obtain the temperature of the first high-frequency electrode 110. Although FIG. 4 illustrates only one thermocouple 140, the number of the thermocouples 140 is not limited to one, and a plurality of thermocouples may be arranged if necessary. The thermocouple 140 may be replaced with a Pt resistance temperature detector or a thermistor. However, thermocouples are particularly preferable from the viewpoint of reduction in cost, since inexpensive thermocouples of small size and high accuracy are available.

To efficiently convey the heat generated by the heat-generating chips 120 to the first high-frequency electrode 110, the sealing film 150 covering the heat-generating chips 120 and the like and the first holding member main body 262 located therearound preferably have low thermal conductivity. Specifically, the thermal conductivity of the sealing film 150 is preferably lower than the thermal conductivities of the first high-frequency electrode 110 and the board 121. Since the sealing film 150 and the first holding member main body 262 have low thermal conductivity, thermal conduction is achieved with small loss.

In the present embodiment, for example, the first high-frequency electrode 110 has a longitudinal length of about 35 mm, and a width of about 7 mm. The cutter-guide groove 264 having a width of about 1 mm is provided along the central axis of the first high-frequency electrode 110.

As illustrated in FIG. 7, the energy source 214 includes a controller 180, a high-frequency energy output circuit 181, a heat-generating-chip driving circuit 182, a heat-generating-chip temperature obtaining circuit 183, a thermocouple-temperature obtaining circuit 184, an input module 185, a display module 186, a storage module 187, and a speaker 188. The controller 180 is connected to the modules in the energy source 214, and controls the modules in the energy source 214. The high-frequency energy output circuit 181 is connected with the energy treatment tool 212, and drives the first high-frequency electrode 110 and the second high-frequency electrode 115 of the energy treatment tool 212 under the control of the controller 180. Specifically, the high-frequency energy output circuit 181 applies a high-frequency voltage to the first high-frequency electrode 110 and the second high-frequency electrode 115 via the high-frequency electrode conducting wire 268.

The heat-generating-chip driving circuit 182 is connected with the energy treatment tool 212, and drives the heat-generating chips 120 of the energy treatment tool 212 under the control of the controller 180. Specifically, under the control of the controller 180, the heat-generating-chip driving circuit 182 supplies electric power for heating to the heat-generating members 122 of the heat-generating chips 120 through the heat-generating chip conducting wires 161. In the operation, the heat-generating-chip driving circuit 182 can change the amount of the electric power supplied to the heat-generating chips 120.

The heat-generating-chip temperature obtaining circuit 183 is connected with the heat-generating chips 120 through the heat-generating chip conducting wires 161. The heat-generating-chip temperature obtaining circuit 183 has a function of obtaining the resistance of the heat-generating member 122 of the heat-generating chip 120, based on the voltage applied to the heat-generating chip 120 and the electric current flowing in the operation. The resistance of the heat-generating member 122 changes according to the temperature of the heat-generating member 122. The relation between the temperature of the heat-generating member 122 and the resistance of the heat-generating member 122 is obtained in advance, and the relation is stored in the storage module 187 in advance. The heat-generating-chip temperature obtaining circuit 183 obtains the relation between the temperature and the resistance of the heat-generating member 122 via the controller 180, and obtains the temperature of the heat-generating member 122 based on the resistance of the heat-generating member 122. Since the temperature of the heat-generating member 122 is obtained based on the resistance thereof, it is unnecessary to separately provide a temperature-measuring device for measuring the temperature of the heat-generating member 122. The heat-generating-chip temperature obtaining circuit 183 outputs the obtained temperature of the heat-generating member 122 to the controller 180. As a matter of course, the heat-generating-chip temperature obtaining circuit 183 may include a memory, and the memory may store the relation between the temperature and the resistance of the heat-generating member 122, instead of the storage module 187. By adopting the above configuration, the heat-generating-chip temperature obtaining circuit 183 can obtain the temperature of the heat-generating member 122, without accessing the storage module 187 via the controller 180.

The thermocouple temperature obtaining circuit 184 is connected with the thermocouple 140 through the cable 228, and obtains the temperatures of the first high-frequency electrode 110 and the second high-frequency electrode 115. The thermocouple temperature obtaining circuit 184 outputs the obtained temperature to the controller 180.

The controller 180 is connected with the foot switch (SW) 216, and receives an ON signal for starting treatment with the energy treatment tool 212 and an OFF signal for stopping treatment, from the foot switch 216. The input module 185 inputs various settings for the controller 180. The display module 186 displays various settings for the controller 180. The storage module 187 stores various data items necessary for operation of the energy source 214. The speaker 188 outputs an alarm sound and the like.

As described above, for example, the first high-frequency electrode 110 or the second high-frequency electrode 115 functions as a heat-transfer member that contacts the biotissue and transfers heat to the biotissue. For example, the heat-generating chips 120 function as heat-generating chips that heat the heat-transfer member. For example, the heat-generating members 122 function as heat-generating members formed on the heat-generating chips. For example, the heat-generating members 122 and the heat-generating-chip temperature obtaining circuit 183 function as a first temperature-measuring module that obtains the temperature of the heat-generating members as a first temperature. For example, the thermocouple 140 functions as a temperature-measuring element disposed in a region with which the heat-generating chip of the heat-transfer member is not connected. For example, the thermocouple temperature obtaining circuit 184 functions as a second temperature-measuring module that obtains the temperature measured by the temperature-measuring element as a second temperature. For example, the controller 180 functions as a controller that determines the supplied electric power.

Next, operation of the treatment device 210 according to the present embodiment will be explained hereinafter. The operator operates the input module 185 of the energy source 214 in advance, to set the output conditions for the treatment device 210, such as the electric power Pset [W] of the high-frequency energy output, the target temperature Tset [° C.] of the thermal energy output, and the treatment time $t_{op}$ [sec]. It may be configured to individually set the values, or configured to select a set of set values according to the surgical procedure.

The holder 226 and the shaft 224 of the energy treatment tool 212 are inserted into the abdominal cavity through, for example, the abdominal wall. The operator operates the operating knobs 232 to open and close the holder 226, and holds the biotissue to be treated with the first holding member 260 and the second holding member 270. In the operation, the biotissue to be treated contacts both the first high-frequency electrode 110 provided on the first holding member 260 and the second high-frequency electrode 115 provided on the second holding member 270.

When the biotissue to be treated is held with the holder 226, the operator operates the foot switch 216. When the foot switch 216 is switched to the ON state, a high-frequency electric power of a preset electric power Pset [W] is supplied from the high-frequency energy output circuit 181 of the energy source 214 to the first high-frequency electrode 110 and the second high-frequency electrode 115 through the cable 228 and the high-frequency electrode conducting wire 268. The supplied electric power is, for example, about 20 [W] to 80 [W]. As a result, the biotissue generates heat, and the tissue is cauterized. The cautery denatures and coagulates the tissue.

Next, the energy source 214 stops the output of the high-frequency energy, and then supplies electric power from the heat-generating-chip driving circuit 182 to the heat-generating chips 120, such that the temperatures of the first high-frequency electrode 110 and the second high-frequency electrode 115 reach the target temperature Tset [° C.]. The target temperature Tset is, for example, 100 [° C.]

to 300 [° C.]. In the operation, the electric current flows through the heat-generating chips 120, from the heat-generating-chip driving circuit 182 of the energy source 214 via the cable 228 and the heat-generating chip conducting wires 161. The heat-generating member 122 of each heat-generating chip 120 generates heat by the electric current.

The heat generated by the heat-generating member 122 disposed in the first high-frequency electrode 110 is conveyed to the first high-frequency electrode 110. As a result, the temperature of the first high-frequency electrode 110 increases. In the same manner, the temperature of the second high-frequency electrode 115 is increased by the heat generated by the electric current flowing through the heat-generating chip 120 disposed in the second high-frequency electrode 115. As detailed below, the controller 180 performs feedback control for the electric power supplied to the heat-generating chips 120, based on the temperatures of the heat-generating members 122 obtained from the heat-generating-chip temperature obtaining circuit 183, or the temperatures of the first high-frequency electrode 110 and the second high-frequency electrode 115 obtained by the thermocouple 140 and obtained from the thermocouple temperature obtaining circuit 184. Thereby, the controller 180 controls the temperatures of the first high-frequency electrode 110 and the second high-frequency electrode 115 to the target temperature Tset [° C.].

As a result of an increase in temperature of the first high-frequency electrode 110 and the second high-frequency electrode 115, the biotissue contacting the first high-frequency electrode 110 or the second high-frequency electrode 115 is further cauterized and further coagulated. When the biotissue is coagulated by heating, the output of the thermal energy is stopped. Lastly, the operator operates the operating knobs 232 to move the cutter 254, and cuts the biotissue. As described above, the treatment of the biotissue is finished.

The first high-frequency electrode 110 and the second high-frequency electrode 115 are configured in the same manner, as a pair. The heat-generating unit 100 including the first high-frequency electrode 110 will be explained hereinafter as an example. In the configuration of the present embodiment, the electric power supplied to the heat-generating chip 120 can be adjusted by feedback control based on the temperature obtained by the thermocouple 140, to set the temperature of the first high-frequency electrode 110 to the target temperature Tset. However, adjusting the supplied electric power based on the temperature obtained by the thermocouple 140 may cause the following problem.

The cost for the heat-generating chip 120 strongly depends on the chip size. Thus, it is required to use the heat-generating chip 120 having a small area, to reduce the cost. On the other hand, in use of the treatment device 210, it is required to increase the temperature of the first high-frequency electrode 110 to a desired temperature in a short time from the start of heating. It is necessary to supply much electric power to the heat-generating chip 120 at the early stage of heating, to rapidly increase the temperature of the first high-frequency electrode 110 in a short time by the heat-generating chip 120 having a small area. This structure greatly increases the heat flux density from the heat-generating chip 120 to the first high-frequency electrode 110. Specifically, this structure increases the difference in temperature between the heat-generating chip 120 and the first high-frequency electrode 110.

In view of the above, the temperature of the heat-generating member 122 may become extremely high when the electric power supplied to the heat-generating chip 120 is controlled based on the temperature of the first high-frequency electrode 110 measured by the thermocouple 140. As described above, when the temperature of the heat-generating member 122 becomes extremely high, the temperature around the heat-generating member 122 may exceed the heat resistant temperature of the sealing film 150, or the heat-generating member 122 may be broken. Specifically, the heat-generating unit 100 may break down.

On the other hand, it is possible to control the temperature of the first high-frequency electrode 110 with high accuracy by using the temperature of the heat-generating member 122, without using the thermocouple 140. However, to perform such control, it is necessary to obtain the temperature of the heat-generating member 122 with high accuracy. It is necessary to manufacture the heat-generating chips 120 with very small variations in resistance, or obtain the relation between the temperature and the resistance for each heat-generating chip, to obtain the temperature of the heat-generating member 122 with high accuracy by the heat-generating-chip temperature obtaining circuit 183 by using the relation between the resistance and the temperature based on the resistance of the heat-generating member 122. Thus, it is difficult to control the temperature of the first high-frequency electrode 110 by using only the temperature of the heat-generating member 122 obtained based on the resistance of the heat-generating member 122. In comparison with this, the thermocouple 140 enables inexpensive and highly accurate temperature measurement.

Figure 8:
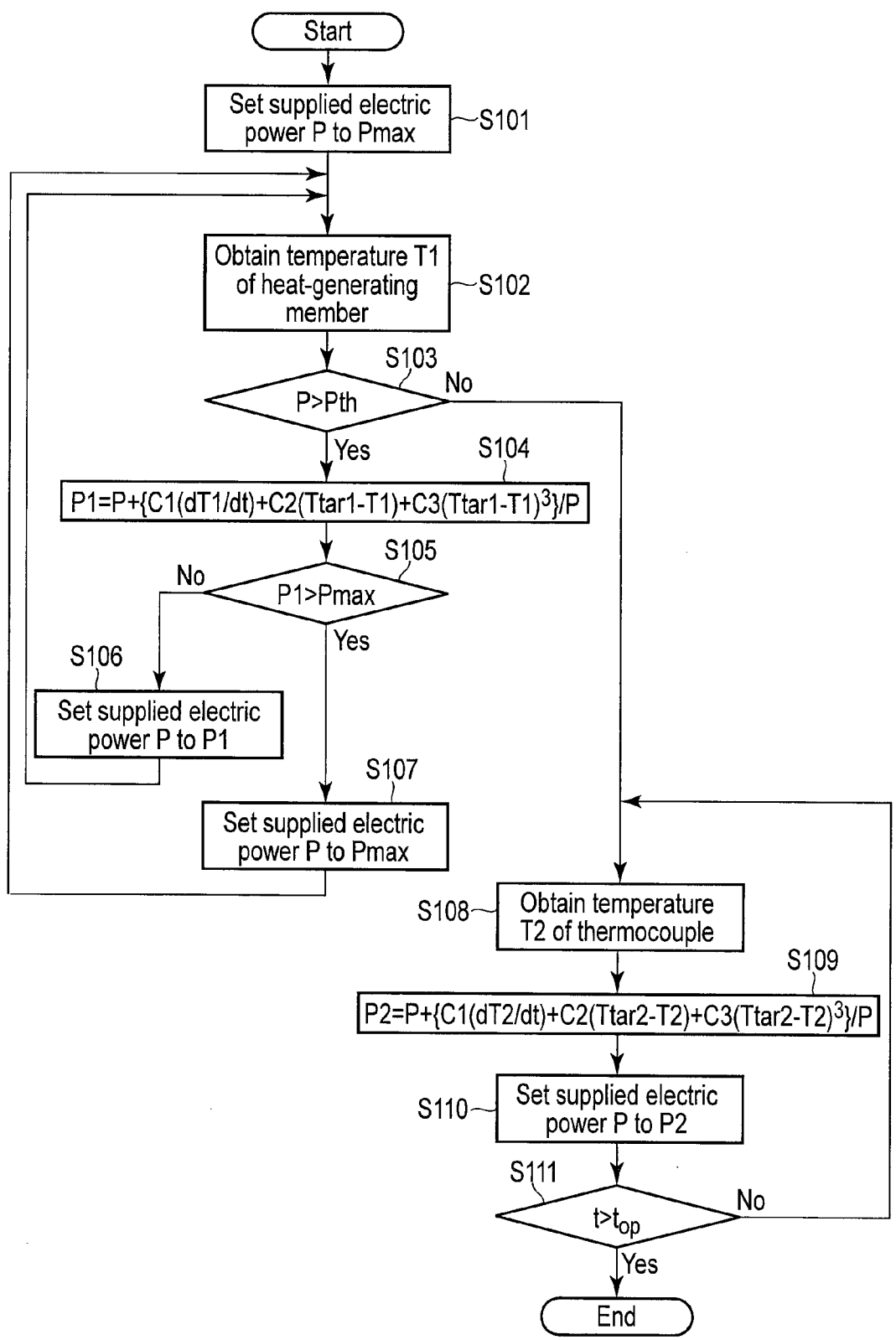
FIG. 8 is a flowchart of an example of processing performed by a controller according to a first embodiment.

Thus, in the present embodiment, the controller 180 controls the temperature of the first high-frequency electrode 110 as follows, by using the temperature of the heat-generating member 122 obtained by the heat-generating-chip temperature obtaining circuit 183, and the temperature of the thermocouple 140 obtained by the thermocouple temperature obtaining circuit 184. FIG. 8 illustrates a flowchart of an operation example of temperature control processing performed by the controller 180.

In Step S101, the controller 180 sets supplied electric power P to be supplied to the heat-generating chip 120 to a preset maximum value Pmax for the supplied electric power. The maximum value Pmax is set to an electric power at which the heat-generating unit 100 is not broken. In Step S102, the controller 180 obtains a temperature T1 of the heat-generating member 122. The temperature T1 of the heat-generating member 122 is calculated by the heat-generating-chip temperature obtaining circuit 183, based on the resistance of the heat-generating member 122, as described above.

In Step S103, the controller 180 determines whether the supplied electric power P is greater than a predetermined threshold Pth or not. When the supplied electric power P is greater than the threshold Pth, the processing goes to Step S104. In Step S104, the controller 180 calculates the supplied electric power P1 with the following expression (1):

$$P1 = P + \{C1(dT1/dt) + C2(Ttar1 - T1) + C3(Ttar1 - T1)^3\}/P, \quad (1)$$

where C1, C2, and C3 are control gains, and Ttar1 is a target temperature in the case where feedback control is performed using the temperature T1 of the heat-generating member 122. The control expression illustrated in expression (1) is an example, and another control expression may be used. For example, C3 may be 0.

In Step S105, the controller 180 determines whether the calculated electric power P1 is greater than the maximum value Pmax or not. When the electric power P1 is not greater than the maximum value Pmax, that is, when the electric power P1 is equal to or less than the maximum value Pmax, the processing goes to Step S106. In Step S106, the controller 180 sets the supplied electric power P to the electric power P1 calculated in Step S104. Thereafter, the processing returns to Step S102.

On the other hand, when the electric power P1 is greater than the maximum value Pmax in the determination in Step S105, the processing goes to Step S107. In Step S107, the controller 180 sets the supplied electric power P supplied to the heat-generating chip 120 to the maximum value Pmax. Thereafter, the processing returns to the Step S102.

When the supplied electric power P is not greater than the threshold Pth in the determination of Step S103, that is, when the supplied electric power P is equal to or less than the threshold Pth, the processing goes to Step S108. In Step S108, the controller 180 obtains the temperature T2 measured by the thermocouple 140 from the thermocouple temperature obtaining circuit 184.

In Step S109, the controller 180 calculates the supplied electric power P2 by the following expression (2):

$$P2 = P + \{C1(dT2/dt) + C2(Ttar2 - T2) + (C3(Ttar2 - T2)^3\}/P, \quad (2)$$

where Ttar2 is a target temperature in the case of performing feedback control using the temperature T2 of the thermocouple 140. For example, the target temperature Ttar2 is the above target temperature Tset.

In Step S110, the controller 180 sets the supplied electric power P to the electric power P2 calculated in Step S109. Thereafter, the processing goes to Step S111. In Step S111, the controller 180 determines whether an elapsed time t from the start of heating is greater than the above treatment time $t_{op}$ or not. When the elapsed time t is greater than the treatment time $t_{op}$, the processing is ended. On the other hand, when the elapsed time t is not greater than the treatment time $t_{op}$, that is, when the elapsed time t is equal to or less than the treatment time $t_{op}$, the processing returns to Step S108.

Figure 9A:
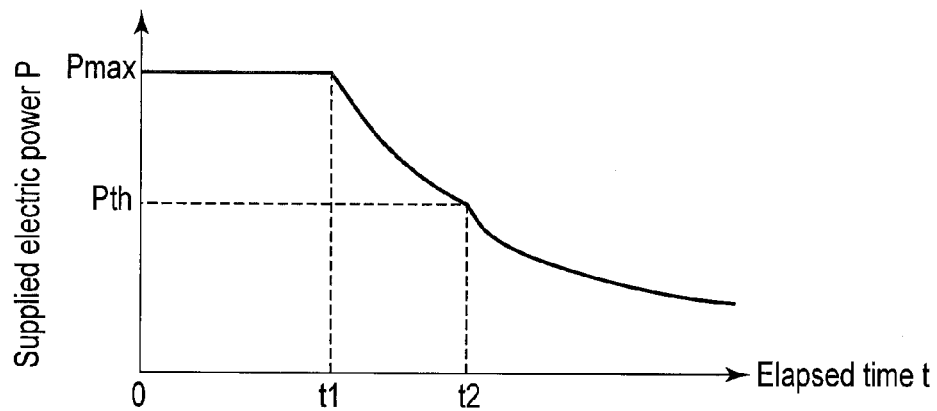
FIG. 9A is a schematic diagram of an example of a relation between the elapsed time and the supplied electric power.
Figure 9B:
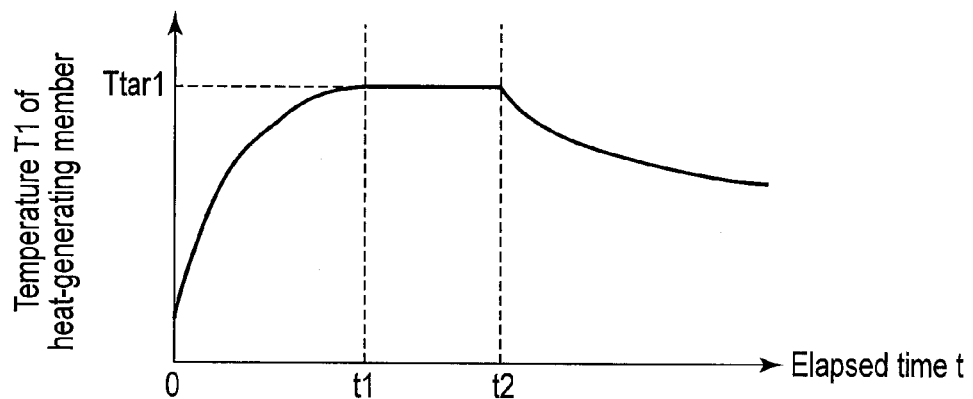
FIG. 9B is a schematic diagram of an example of relation between the elapsed time and the temperature of the heat-generating member.
Figure 9C:
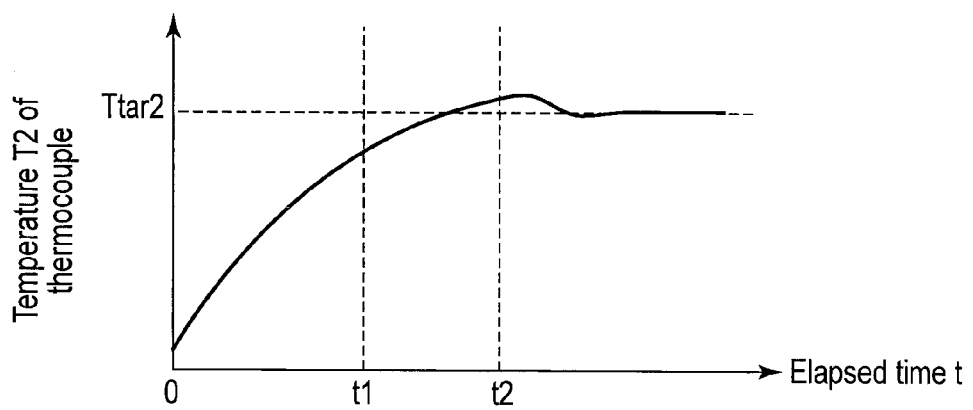
FIG. 9C is a schematic diagram of an example of a relation between the elapsed time and the temperature of a thermocouple.

FIG. 9A is a schematic diagram of a relation of the supplied electric power P to the elapsed time t, FIG. 9B is a schematic diagram of a relation of the temperature T1 of the heat-generating member 122 to the elapsed time t, and FIG. 9C is a schematic diagram of a relation of the temperature T2 of the thermocouple 140 to the elapsed time t.

At the time directly after heating is started, the supplied electric power P is set to Pmax being the maximum value, as illustrated in FIG. 9A. When the electric power is supplied to the heat-generating member 122, the temperature T1 of the heat-generating member 122 gradually increases as illustrated in FIG. 9B. During this time, the electric power P1 is calculated in Step S104 in accordance with the above expression (1). When the calculated electric power P1 is greater than the maximum value Pmax, the supplied electric power P is set to the maximum value Pmax in Step S107. Thus, for a period of time after the start of heating, the supplied electric power P is set to the maximum value Pmax. When the electric power P1 calculated in Step S104 in accordance with the expression (1) becomes equal to or less than the maximum value Pmax, the supplied electric power P is set to electric power P1 in Step S106. During the operation, the temperature T2 measured by the thermocouple 140 also gradually increases as illustrated in FIG. 9C.

In the course of time, the temperature T1 of the heat-generating member 122 reaches the target temperature Ttar1. The elapsed time t at the time is illustrated as t1 in FIG. 9A, FIG. 9B, and FIG. 9C. After the temperature T1 of the heat-generating member 122 has reached the target temperature Ttar1, the controller 180 sets the electric power P1 calculated in accordance with the expression (1) such that the temperature T1 of the heat-generating member 122 is maintained at the target temperature Ttar1, as the supplied electric power P in Step S106. Since the calculation is performed in accordance with the expression (1), the supplied electric power P gradually decreases, as illustrated in FIG. 9A. When the supplied electric power P gradually decreases, the temperature T1 of the heat-generating member 122 is maintained at the target temperature Ttar1. The temperature T2 of the thermocouple 140 gradually increases as illustrated in FIG. 9C, while the controller 180 repeats the processing of Step S102 to Step S107.

In the course of time, when the supplied electric power P becomes equal to or less than the predetermined threshold Pth, the processing goes to Step S108. The elapsed time t at the time is illustrated as t2 in FIG. 9A, FIG. 9B, and FIG. 9C. As described above, the processing of Step S102 to Step S107 is performed from the start of heating to the time t2, such that the temperature T1 of the heat-generating member 122 reaches the target temperature Ttar1.

During the time from the start of heating to the time t2, in which the processing of Step S102 to Step S107 is performed, the heat-generating-chip temperature obtaining circuit 183 obtains the temperature T1 of the heat-generating member 122, by using the relation between the resistance of the heat-generating member 122 and the temperature of the heat-generating member 122 for the resistance. As described above, it is difficult to obtain the temperature T1 of the heat-generating member 122 by such a method with high accuracy. Thus, in the present embodiment, no high accuracy is required for obtaining the temperature T1 of the heat-generating member 122. Thus, the target temperature Ttar1 is set in consideration of the fact that the temperature T1 of the heat-generating member 122 includes an error.

After the time t2, the controller 180 performs feedback control with the electric power P2 calculated in accordance with the expression (2), such that the temperature T2 of the thermocouple 140 becomes the target temperature Ttar2. Since the temperature T2 is measured by the thermocouple 140 with high accuracy, the temperature of the first high-frequency electrode 110 can be controlled to the target temperature Tset with high accuracy, by setting the target temperature Tset optimum for the treatment to the target temperature Ttar2. The controller 180 repeats the processing of Step S108 to Step S111, until the elapsed time t reaches the treatment time $t_{op}$. As described above, the temperature of the first high-frequency electrode 110 is maintained at the target temperature Tset, until the treatment, time reaches the time $t_{op}$ thereafter.

As described above, for example, the time t2 corresponds to a transition point in time. For example, the time period from the start of heating to the time t2 corresponds to a first time region. For example, the time period after the time t2 corresponds to a second time region. For example, the temperature T1 of the heat-generating member 122 corresponds to a first temperature. For example, the temperature T2 of the thermocouple 140 corresponds to a second temperature.

In the present embodiment, feedback control using the temperature T1 of the heat-generating member 122 switches to feedback control using the temperature T2 of the thermocouple 140. The temperature of the heat-generating member 122 is always higher than the temperature of the first high-frequency electrode 110, and the difference in temperature between the heat-generating member 122 and the first high-frequency electrode 110 increases as the supplied electric power increases. In view of these points, the target temperature Ttar1 and the threshold Pth are set to proper values. Thereby, the following effect is obtained.

Specifically, the target temperature Ttar1 is set lower than the limits of heat resistance of the sealing film 150 and a temperature at which the heat-generating member 122 is broken. Setting the target temperature Ttar1 as described above prevents exceeding the limits of heat resistance of the sealing film 150, and breakage of the heat-generating member 122. On the other hand, a large amount of electric power can be safely supplied to the heat-generating chip 120, by setting the target temperature Ttar1 to a temperature as high as possible within a range satisfying the above conditions. As a result, it is possible to increase the temperature of the first high-frequency electrode 110 in a short time.

In addition, the threshold Pth is set to an electric power amount such that the difference between the temperature T1 of the heat-generating member 122 and the temperature T2 of the thermocouple 140 is equal to the difference between the target temperature Ttar1 and the target temperature Ttar2. By such a setting, the temperature T1 of the heat-generating member 122 can be maintained at the target temperature Ttar1 for a longer time, and the temperature of the first high-frequency electrode 110 can be prevented from being much higher than the target temperature Ttar2.

As described above, according to the present embodiment, the temperature of the first high-frequency electrode 110 can be increased in a short time, by safely supplying a large amount of electric power at the early stage of heating without incurring malfunction of the device. In addition, the temperature of the first high-frequency electrode 110 can be controlled based on a highly accurate result of temperature measurement using the thermocouple 140, in the greater part of the necessary treatment time.

No cost increase due to the requirement for high accuracy is caused when obtaining the temperature T1 of the heat-generating member 122 by the heat-generating-chip temperature obtaining circuit 183. On the other hand, high accuracy at low cost for obtaining the temperature T2 can be achieved by the thermocouple temperature obtaining circuit 184 and the thermocouple 140. As a result, according to the present embodiment, it is possible to achieve a treatment device that performs highly accurate temperature control without causing malfunction of the whole system, at small cost.

Although the supplied electric power P is used in the present embodiment as an index for switching feedback control using the temperature T1 of the heat-generating member 122 to feedback control using the temperature T2 of the thermocouple 140, such structure is not limited thereto. For example, the voltage or electric current applied to the heat-generating chip 120 may be used as the index. However, it is preferable to use the supplied electric power P, since the difference in temperature between the heat-generating member 122 and the first high-frequency electrode 110 mainly depends on the supplied electric power P as described above. In addition, although the same controls gains C1, C2, and C3 are used in the expression (1) and the expression (2), control gains of different values may be used.

In addition, the supplied electric power P sharply fluctuates in a period (first time region) in which feedback control using the temperature T1 of the heat-generating member 122 is performed. In comparison with this, the supplied electric power P incurs relatively small fluctuations in a period (second time region) in which feedback control using the temperature T2 of the thermocouple 140 is performed. Thus, in the second time region, the sampling rate of the feedback control may be set lower than that of the first time region. In the present embodiment using the thermocouple, using a lower sampling rate in the second time region is preferable from the point of view of performing highly accurate temperature measurement, since a longer integral time of temperature measurement can be secured. On the other hand, it is preferable to use a higher sampling rate in the first time region, since the supplied electric power P sharply fluctuates in the first time region.

Second Embodiment

A second embodiment will be explained hereinafter. In the following explanation, points that are different from the first embodiment will be described, and like constituent elements are denoted by like reference numerals, with explanation thereof omitted. The structure of a treatment device 210 according to the present embodiment is the same as the first embodiment.

The present embodiment is different from the first embodiment in the condition for switching feedback control using the temperature T1 of the heat-generating member 122 to feedback control using the temperature T2 of the thermocouple 140, in temperature control performed by the controller 180. The condition in the present embodiment is that the difference T1-T2 in temperature between the heat-generating member 122 and the thermocouple 140 becomes equal to or less than a threshold Tth1, while the condition in the first embodiment is that the supplied electric power P becomes equal to or less than the threshold Pth.

FIG. 10 illustrates a flowchart of temperature control performed by a controller 180 according to the present embodiment. In Step S201, the controller 180 sets a supplied electric power P supplied to a heat-generating chip 120 to a preset maximum value Pmax of the supplied electric power. In Step S202, the controller 180 obtains a temperature T1 of a heat-generating member 122 and a temperature T2 of a thermocouple 140.

In Step S203, the controller 180 determines whether a difference T1-T2 in temperature between the temperature T1 of the heat-generating member 122 and the temperature T2 of the thermocouple 140 is greater than a predetermined threshold Tth1 or not. When the difference T1-T2 is greater than the threshold Tth1, the processing goes to Step S204.

The controller 180 calculates an electric power P1 to be supplied by the expression (1) in Step S204, in the same manner as the first embodiment. When it is determined in Step S205 that the calculated electric power P1 is equal to or less than the maximum value Pmax, the controller sets the supplied electric power P to the electric power P1 in Step S206. When it is determined that the supplied electric power P is greater than the maximum value Pmax, the controller sets the supplied electric power P to the maximum value Pmax in Step S207. In either case, the processing returns to Step S202.

On the other hand, when the difference T1-T2 is equal to or less than the threshold Tth1 in the determination of Step S203, the processing goes to Step S208. In the same manner as the first embodiment, the controller obtains the temperature T2 of the thermocouple 140 in Step S208, calculates an electric power P2 to be supplied by the expression (2) in Step S209, and sets the supplied electric power P to the electric power P2 in Step S210. These operations are repeated until the elapsed time t reaches the treatment time $t_{op}$.

The same effect as the first embodiment can be obtained, by setting the threshold Tth to a proper value, since the difference T1-T2 depends on the supplied electric power P as described in the explanation of the first embodiment.

Third Embodiment

A third embodiment will be explained hereinafter. In the following explanation, points that are different from the first embodiment will be described, and like constituent elements are denoted by like reference numerals, with explanation thereof omitted. The structure of a treatment device 210 according to the present embodiment is the same as the first embodiment.

The present embodiment is different from the first embodiment in the condition for switching feedback control using the temperature T1 of the heat-generating member 122 to feedback control using the temperature T2 of the thermocouple 140, in temperature control performed by the controller 180. The condition in the present embodiment is that the temperature T2 of the thermocouple 140 becomes equal to or greater than a threshold Tth2, while the condition in the first embodiment is that the supplied electric power P becomes equal to or less than the threshold Pth.

Figure 11:
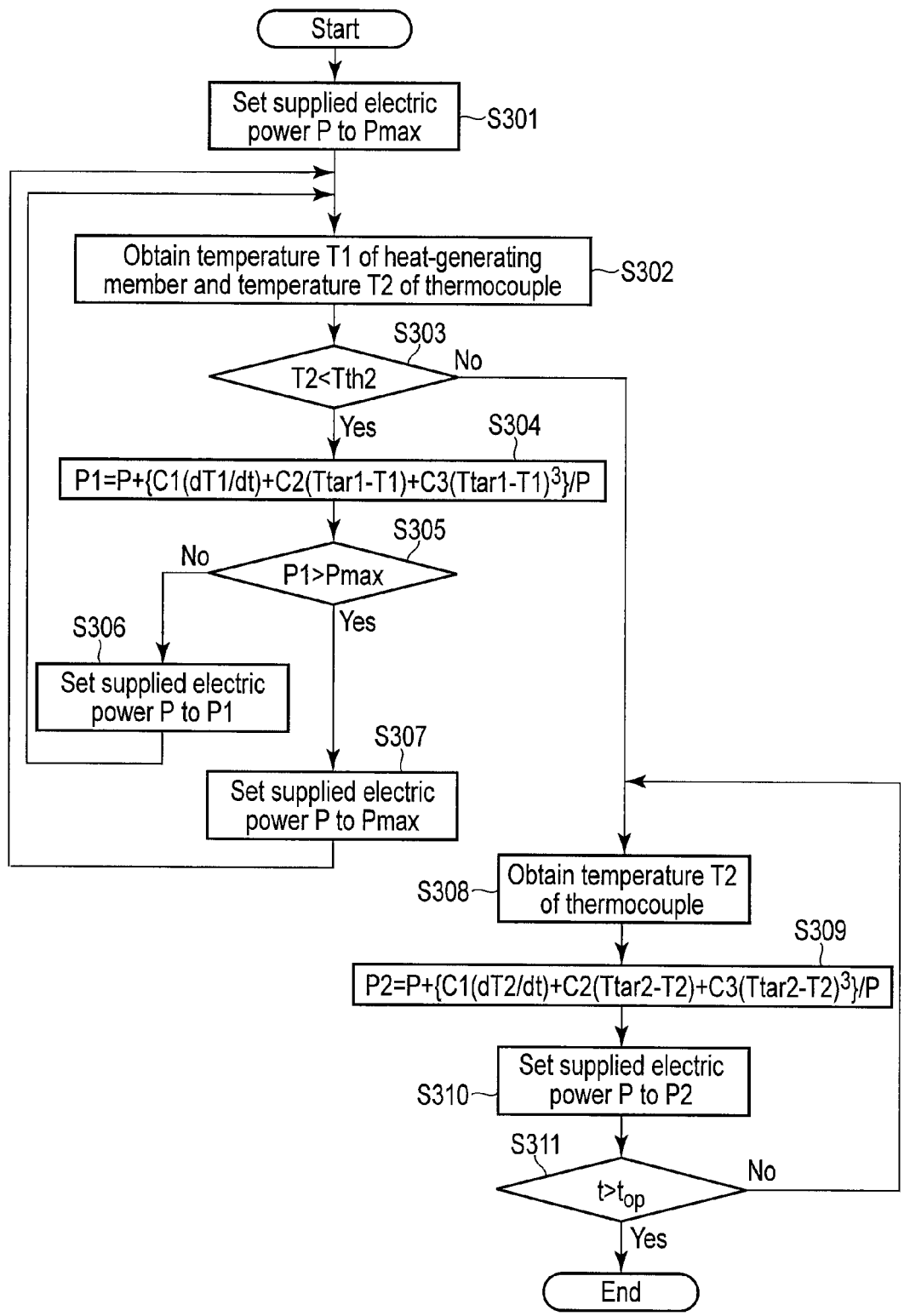
FIG. 11 is a flowchart of an example of processing performed by a controller according to a third embodiment.

FIG. 11 illustrates a flowchart of temperature control performed by a controller 180 according to the present embodiment. In Step S301, the controller 180 sets a supplied electric power P supplied to a heat-generating chip 120 to a preset maximum value Pmax of the supplied electric power. In Step S302, the controller 180 obtains a temperature T1 of a heat-generating member 122 and a temperature T2 of a thermocouple 140.

In Step S303, the controller 180 determines whether the temperature T2 of the thermocouple 140 is less than a predetermined threshold Tth2 or not. When the temperature T2 of the thermocouple 140 is less than the threshold Tth2, the processing goes to Step S304.

The controller 180 calculates an electric power P1 to be supplied by the expression (1) in Step S304, in the same manner as the first embodiment. When it is determined in Step S305 that the calculated electric power P1 is equal to or less than the maximum value Pmax, the controller sets the supplied electric power P to the electric power P1 in Step S306. When it is determined that the supplied electric power P is greater than the maximum value Pmax, the controller sets the supplied electric power P to the maximum value Pmax in Step S307. In either case, the processing returns to Step S302.

On the other hand, when the temperature of the thermocouple 140 is equal to or greater than the threshold Tth2 in the determination of Step S303, the processing goes to Step S308. In the same manner as the first embodiment, the controller obtains the temperature T2 of the thermocouple 140 in Step S308, calculates an electric power P2 to be supplied by the expression (2) in Step S309, and sets the supplied electric power P to the electric power P2 in Step S310. These operations are repeated until the elapsed time t reaches the treatment time $t_{op}$.

The same effect as the first embodiment can be obtained by setting the threshold Tth2 to a proper value in a treatment device in which a difference in thermal load between objects to be heated is small, although the temperature T1 of the heat-generating member 122 in the case where the temperature T2 of the thermocouple 140 is equal to or greater than the threshold Tth2 differs according to the thermal load of the object to be heated.

Fourth Embodiment

A fourth embodiment will be explained hereinafter. In the following explanation, points that are different from the first embodiment will be described, and like constituent elements are denoted by like reference numerals, with explanation thereof omitted. The structure of a treatment device 210 according to the present embodiment is the same as the first embodiment.

The present embodiment is different from the first embodiment in the condition for switching feedback control using the temperature T1 of the heat-generating member 122 to feedback control using the temperature T2 of the thermocouple 140, in temperature control performed by the controller 180. The condition in the present embodiment is that the elapsed time t becomes equal to or greater than a threshold $t_{th}$, while the condition in the first embodiment is that the supplied electric power P becomes equal to or less than the threshold Pth.

FIG. 12 illustrates a flowchart of temperature control performed by a controller 180 according to the present embodiment. In Step S401, the controller 180 sets a supplied electric power P supplied to a heat-generating chip 120 to a preset maximum value Pmax of the supplied electric power. In Step S402, the controller 180 obtains a temperature T1 of a heat-generating member 122.

In Step S403, the controller 180 determines whether the elapsed time t is less than a predetermined threshold $t_{th}$ or not. When the elapsed time t is less than the threshold $t_{th}$, the processing goes to Step S404.

The controller 180 calculates an electric power P1 to be supplied by the expression (1) in Step S404, in the same manner as the first embodiment. When it is determined in Step S405 that the calculated electric power P1 is equal to or less than the maximum value Pmax, the controller sets the supplied electric power P to the electric power P1 in Step S406. When it is determined that the supplied electric power P is greater than the maximum value Pmax, the controller sets the supplied electric power P to the maximum value Pmax in Step S407. In either case, the processing returns to Step S402.

On the other hand, when the elapsed time t is equal to or greater than the threshold $t_{th}$ in the determination of Step S403, the processing goes to Step S408. In the same manner as the first embodiment, the controller obtains the temperature T2 of the thermocouple 140 in Step S408, calculates an electric power P2 to be supplied by the expression (2) in Step S409, and sets the supplied electric power P to the electric power P2 in Step S410. These operations are repeated until the elapsed time t reaches the treatment time $t_{op}$.

The same effect as the first embodiment can be obtained by setting the threshold $t_{th}$ to a proper value, in a treatment device in which a difference in heat load between objects to be heated is small, like the third embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device configured to treat a biotissue by heating the biotissue to a target temperature, the treatment device comprising:
    a heat-transfer member configured to contact and heat the biotissue;
    a heat generating member comprising a resistance heater configured to heat the heat-transfer member by an electric power supplied to the resistance heater;
    a temperature-measuring sensor associated with the heat-transfer member to obtain a first temperature of the heat-transfer member; and
    a controller configured to:
        obtain a second temperature of the resistance heater based on a value of a resistance of the resistance heater;
        determine whether the electric power supplied to the resistance heater is greater than a predetermined threshold, and
        switch control between a first control performed when the electric power supplied to the resistance heater is determined to be greater than the predetermined threshold and a second control performed when the electric power supplied to the resistance heater is determined to be less than the predetermined threshold,
    wherein the first control calculates the electric power supplied to the resistance heater based on the second temperature, and
    the second control calculates the electric power supplied to the resistance heater based on the first temperature.

2. The treatment device according to claim 1, wherein a sampling rate at which the controller obtains the second temperature is higher than a sampling rate at which the temperature-measuring sensor obtains the first temperature.

3. The treatment device according to claim 1, further comprising a flexible board, wherein the resistance heater is arranged on a first surface of the flexible board.

4. The treatment device according to claim 3, wherein the heat-transfer member is arranged on a second surface of the flexible board.

5. The treatment device according to claim 1, further comprising a wire connected to the heat-transfer member for providing high-frequency power to the heat-transfer member.

6. The treatment device according to claim 1, wherein the controller is further configured to switch control to the second control when the electric power supplied to the resistance heater is determined to be equal to the predetermined threshold.

* * * * *